(12) United States Patent
Biftu et al.

(10) Patent No.: US 7,906,649 B2
(45) Date of Patent: Mar. 15, 2011

(54) AMINOCYCLOHEXANES AS DIPEPTIDYL PEPTIDASE-IV INHIBITORS FOR THE TREATMENT OF DIABETES

(75) Inventors: Tesfaye Biftu, Freehold, NJ (US); Danqing Feng, Branchburg, NJ (US); Xiaoxia Qian, New York, NJ (US); Ann E. Weber, Scotch Plains, NJ (US); Jason Cox, East Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 412 days.

(21) Appl. No.: 11/920,038

(22) PCT Filed: May 19, 2006

(86) PCT No.: PCT/US2006/019598
§ 371 (c)(1),
(2), (4) Date: Nov. 7, 2007

(87) PCT Pub. No.: WO2006/127530
PCT Pub. Date: Nov. 30, 2006

(65) Prior Publication Data
US 2009/0105284 A1 Apr. 23, 2009

Related U.S. Application Data

(60) Provisional application No. 60/684,567, filed on May 25, 2005.

(51) Int. Cl.
| | |
|---|---|
| C07D 513/02 | (2006.01) |
| C07D 513/00 | (2006.01) |
| C07D 498/00 | (2006.01) |
| C07D 403/02 | (2006.01) |
| C07D 487/02 | (2006.01) |
| C07D 209/44 | (2006.01) |
| A61K 31/425 | (2006.01) |
| A61K 31/42 | (2006.01) |
| A61K 31/415 | (2006.01) |
| A61K 31/40 | (2006.01) |

(52) U.S. Cl. ..... 546/117; 548/153; 548/218; 548/303.1; 548/360.5; 548/453; 548/471; 514/367; 514/375; 514/387; 514/393; 514/405; 514/406; 514/412; 514/866

(58) Field of Classification Search ............... 546/117; 548/153, 218, 303.1, 360.5, 453, 471; 514/406, 514/405, 367, 393, 375, 387, 412, 866
See application file for complete search history.

(56) References Cited

U.S. PATENT DOCUMENTS

| | | | |
|---|---|---|---|
| 3,174,901 A | 3/1965 | Sterne et al. | |
| 5,654,318 A | 8/1997 | Takemura et al. | |
| 6,699,871 B2 | 3/2004 | Edmondson et al. | |
| 7,482,336 B2 * | 1/2009 | Biftu et al. | 514/211.03 |
| 7,750,034 B2 * | 7/2010 | Biftu et al. | 514/406 |
| 2007/0254865 A1 | 11/2007 | Biftu et al. | |
| 2008/0076773 A1 | 3/2008 | Cox et al. | |
| 2009/0270467 A1 | 10/2009 | Biftu et al. | |

FOREIGN PATENT DOCUMENTS

| | | |
|---|---|---|
| WO | WO 2006/009886 A1 | 1/2006 |
| WO | WO 2006/039325 A2 | 4/2006 |
| WO | WO 2006/058064 A2 | 6/2006 |
| WO | WO 2006/127530 A2 | 11/2006 |
| WO | WO 2007/024993 A3 | 3/2007 |
| WO | 2007/087231 A2 | 8/2007 |
| WO | 2007/087231 A3 | 8/2007 |

OTHER PUBLICATIONS

Weber, "Dipeptidyl Peptidase IV Inhibitors for the Treatment of Diabetes", Journal of Medicinal Chemistry, vol. 47, No. 17, pp. 4135-4141 (Aug. 2004).*

Gao, YD. et al., "Modeling assisted rational design of novel, potent, and selective pyrrolopyrimidine DPP-4 inhibitors", Bioorganic & Medicinal Chemistry Letters, 2007. pp. 3877-3879, vol. 17.

* cited by examiner

*Primary Examiner* — Kevin Weddington
(74) *Attorney, Agent, or Firm* — Janet E. Fair; John C. Todaro

(57) ABSTRACT

The present invention is directed to novel substituted aminocyclohexanes which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

15 Claims, No Drawings

AMINOCYCLOHEXANES AS DIPEPTIDYL PEPTIDASE-IV INHIBITORS FOR THE TREATMENT OF DIABETES

CROSS REFERENCE TO RELATED APPLICATIONS

This application is the National Stage of International Application No. PCT/US2006/019598, filed. 19 May 2006, which claims the benefit under 35 U.S.C. 119(e) of U.S. Provisional Application No. 60/684,567, filed 25 May 2005.

FIELD OF THE INVENTION

The present invention relates to novel substituted aminocyclohexanes which are inhibitors of the dipeptidyl peptidase-IV enzyme ("DPP-TV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV") enzyme are also under investigation as drugs that may be useful in the treatment of diabetes, and particularly Type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.*, 6: 2745-2748 (1996). The usefulness of DPP-IV inhibitors in the treatment of Type 2 diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively to date, especially for utilities other than diabetes. New compounds are needed so that improved DPP-IV inhibitors can be found for the treatment of diabetes and potentially other diseases and conditions. The therapeutic potential of DPP-IV inhibitors for the treatment of Type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to novel substituted aminocyclohexanes which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to substituted aminocyclohexanes useful as inhibitors of dipeptidyl peptidase-IV. Compounds of the present invention are described by structural formula I:

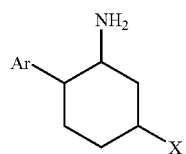

(I)

or a pharmaceutically acceptable salt thereof; wherein
each n is independently 0, 1, 2, or 3;
X is selected from the group consisting of:

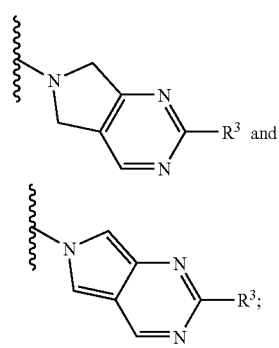

Ar is phenyl unsubstituted or substituted with one to five $R^1$ substituents;
each $R^1$ is independently selected from the group consisting of
  halogen,
  cyano,
  hydroxy,
  $C_{1-6}$ alkyl, unsubstituted or substituted with one to five halogens,
  $C_{1-6}$ alkoxy, unsubstituted or substituted with one to five halogens,
  carboxy,
  $C_{1-6}$ alkyloxycarbonyl,
  amino,
  $NHR^2$,
  $NR^2R^2$,
  $NHSO_2R^2$,
  $NR^2SO_2R^2$,
  $NHCOR^2$,
  $NR^2COR^2$,
  $NHCO_2R^2$,
  $NR^2CO_2R^2$,
  $SO_2R^2$,
  $SO_2NH_2$,
  $SO_2NHR^2$, and
  $SO_2NR^2R^2$;
each $R^2$ is independently $C_{1-6}$ alkyl, unsubstituted or substituted with one to five substituents independently selected from halogen, $CO_2H$, and $C_{1-6}$ alkyloxycarbonyl;
$R^3$ is selected from the group consisting of
  hydrogen,
  hydroxy,
  halogen,
  cyano,
  $CO_2H$,
  $NR^4R^5$,
  $CONR^4R^5$,
  $CH_2CONR^4R^5$,
  $OCONR^4R^5$,
  $SO_2NR^4R^5$,
  $SO_2R^6$,
  $NR^7SO_2R^6$,
  $NR^7CONR^4R^5$,
  $NR^7COR^6$,
  $NR^7CO_2R^6$,
  1H-tetrazol-5-yl,
  $C_{1-6}$ alkyloxycarbonyl,
  $C_{1-6}$ alkyl unsubstituted or substituted with hydroxy or one to five halogens,
  $C_{1-6}$ alkoxy unsubstituted or substituted with hydroxy or one to five halogens,
  $C_{1-6}$ alkylthio,
  $C_{1-6}$ alkylsulfonyl, and
  $(CH_2)_n$—$C_{3-6}$ cycloalkyl, wherein cycloalkyl is unsubstituted or substituted with one to three substituents independently selected from halogen, hydroxy, $C_{1-4}$ alkyl, and $C_{1-4}$ alkoxy, wherein alkyl and alkoxy are unsubstituted or substituted with one to five halogens;
  wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
$R^4$ and $R^5$ are each independently selected from the group consisting of
  hydrogen,
  $(CH_2)_n$-phenyl,
  $(CH_2)_n$—$C_{3-6}$ cycloalkyl, and
  $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;

each $R^6$ is independently $C_{1-6}$ alkyl, wherein alkyl is unsubstituted or substituted with one to five substituents independently selected from halogen and hydroxyl; and $R^7$ is hydrogen or $R^6$.

In one embodiment of the compounds of the present invention, each $R^1$ is independently selected from the group consisting of fluorine, chlorine, bromine, methyl, trifluoromethyl, and trifluoromethoxy.

In a second embodiment of the compounds of the present invention, there are provided compounds of structural formulae Ia and Ib of the indicated stereochemical configuration having a trans orientation of the Ar and $NH_2$ substituents on the two stereogenic cyclohexane carbon atoms marked with an *:

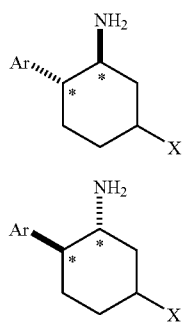

(Ia)

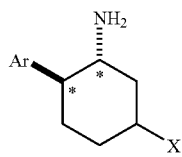

(Ib)

wherein Ar and X are as described above.

In a class of this second embodiment, there are provided compounds of structural formula Ia of the indicated absolute stereochemical configuration having a trans orientation of the Ar and $NH_2$ substituents on the two stereogenic cyclohexane carbon atoms marked with an *:

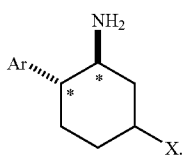

(Ia)

In a second class of this second embodiment, there are provided compounds of structural formulae Ic and Id of the indicated stereochemical configuration having a trans orientation of the Ar and $NH_2$ substituents, a cis orientation of the Ar and X substituents, and a trans orientation of the $NH_2$ and X substituents on the three stereogenic cyclohexane carbon atoms marked with an *:

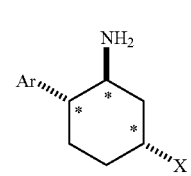

(Ic)

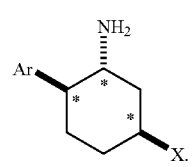

(Id)

In a subclass of this class, there are provided compounds of structural formula Ic of the indicated absolute stereochemical configuration having a trans orientation of the Ar and $NH_2$ substituents, a cis orientation of the Ar and X substituents, and a trans orientation of the $NH_2$ and X substituents on the three stereogenic cyclohexane carbon atoms marked with an *:

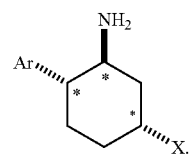

(Ic)

In a third class of this second embodiment, there are provided compounds of structural formulae Ie and If of the indicated stereochemical configuration having a trans orientation of the Ar and $NH_2$ substituents, a trans orientation of the Ar and X substituents, and a cis orientation of the $NH_2$ and X substituents on the three stereogenic cyclohexane carbon atoms marked with an *:

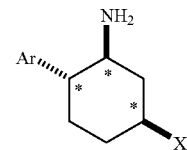

(Ie)

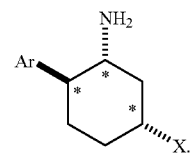

(If)

In a subclass of this class, there are provided compounds of structural formula Ie of the indicated absolute stereochemical configuration having a trans orientation of the Ar and $NH_2$ substituents, a trans orientation of the Ar and X substituents, and a cis orientation of the $NH_2$ and X substituents on the three stereogenic cyclohexane carbon atoms marked with an *:

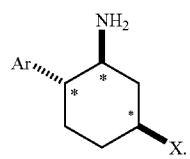

(Ie)

In a subclass of this subclass of the compounds of the present invention, there are provided compounds of structural formulae Ig:

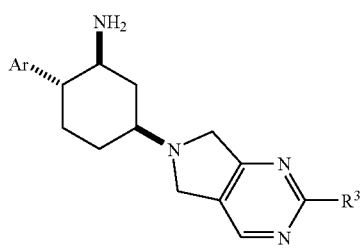

(Ig)

wherein Ar and $R^3$ are as described above.

In another subclass of this subclass of the compounds of the present invention, there are provided compounds of structural formulae Ih:

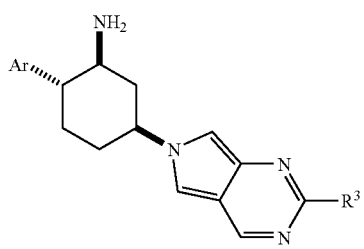

(Ih)

wherein Ar and $R^3$ are as described above.

In a class of compounds of formula Ie, $R^3$ is selected from the group consisting of
hydrogen,
cyano,
$CO_2H$,
1H-tetrazol-5-yl,
$C_{1-3}$ alkyloxycarbonyl,
$CONR^4R^5$,
$CH_2CONR^4R^5$,
$C_{1-3}$ alkyl, wherein alkyl is unsubstituted or substituted with one to five fluorines,
$C_{1-3}$ alkoxy, wherein alkoxy is unsubstituted or substituted with hydroxy or one to five fluorines, and
$C_{3-6}$ cycloalkyl, wherein cycloalkyl is unsubstituted or substituted with one to three substituents independently selected from halogen, hydroxy, $C_{1-4}$ alkyl, and $C_{1-4}$ alkoxy, wherein alkyl and alkoxy are unsubstituted or substituted with one to five halogens.

Nonlimiting examples of compounds of the present invention that are useful as dipeptidyl peptidase-IV inhibitors are the following structures having the indicated absolute stereochemical configurations at the three stereogenic cyclohexane carbon atoms:

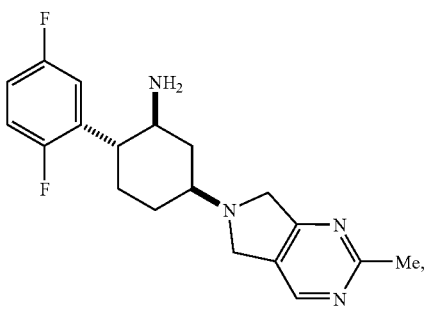

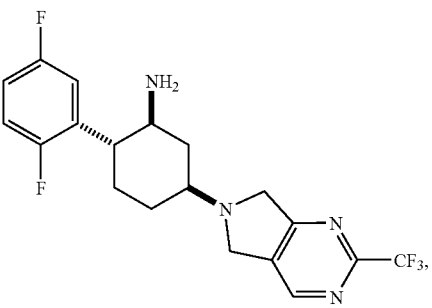

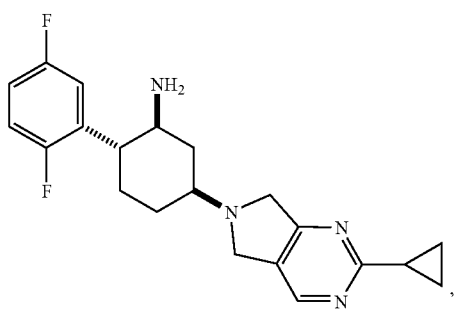

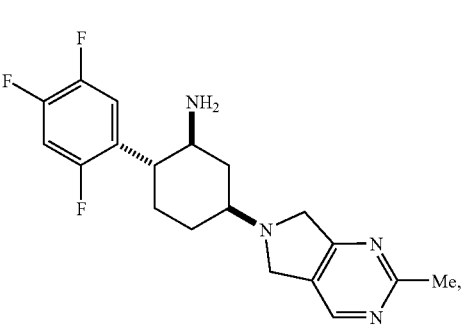

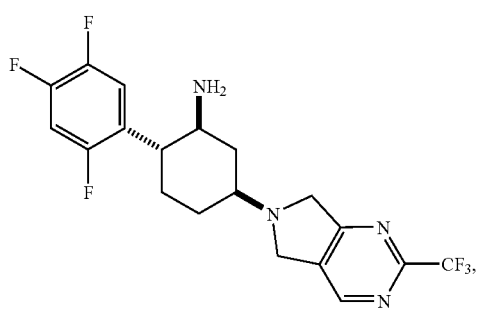

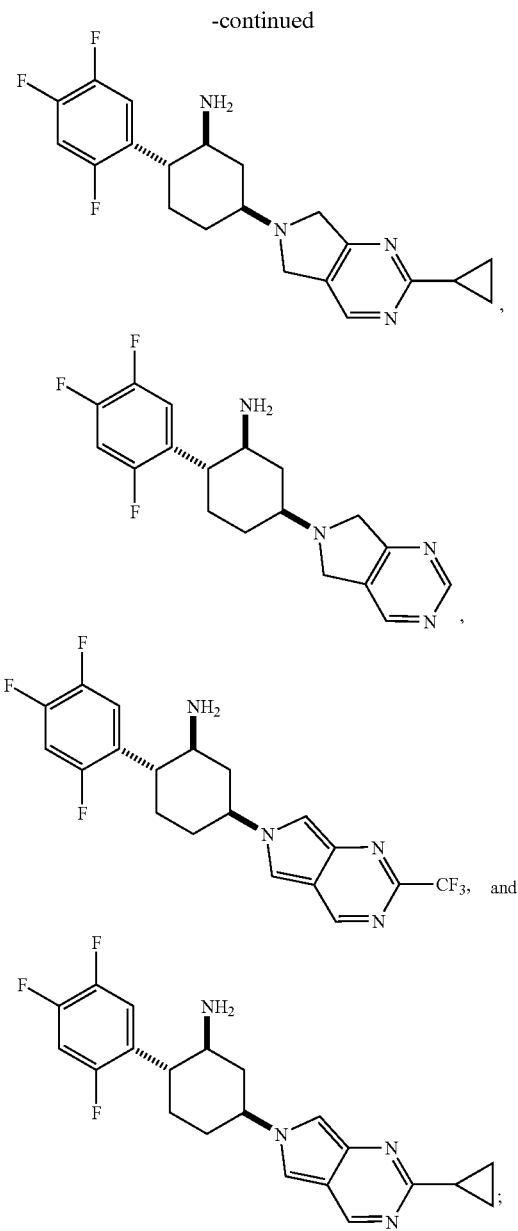

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and SO$_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxypyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1, 2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atoms marked with an * in formulae Ia, Ib, Ic, Id, Ie, and If. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formulae Ia and Ib show the preferred stereochemistry at the stereogenic carbon atoms to which are attached the $NH_2$ and Ar groups on the cyclohexane ring. Formulae Ic, Id, Ie, and If show the preferred stereochemistry at the stereogenic carbon atoms to which are attached the $NH_2$, Ar, and X groups on the cyclohexane ring.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m=50$ μM; $k_{cat}=75$ s$^{-1}$; $k_{cat}/K_m=1.5\times10^6$ M$^{-1}$s$^{-1}$. A typical reaction contains approximately 50 pM enzyme, 50 μM Gly-Pro-AMC, and buffer (100 mM HEPES, pH 7.5, 0.1 mg/ml BSA) in a total reaction volume of 100 μl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an IC$_{50}$ of less than about 1 μM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis. The DPP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine.* 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine* 6: 802-807 (2000)). In addition, studies with DPP-IV deficient mice suggest that these animals are resistant to diet-induced obesity and associated pathology (e.g. hyperinsulinemia).

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[344]; this is prevented by the DPP-IV inhibitor diprotin A; and (3) GRF [3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-IV, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation*, 63: 1495-1500 (1997)). DPP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DPP-IV is upregulated in a number of autoimmune diseases including rheumatoid arthritis, multiple sclerosis, Graves' disease, and Hashimoto's thyroiditis (*Immunology Today*. 20: 367-375 (1999)).

HIV Infection: DPP-IV inhibition may be useful for the treatment or prevention of HIV infection or AIDS because a number of chemokines which inhibit HIV cell entry are potential substrates for DPP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DPP-IV would be expected to decrease HIV infectivity.

Hematopoiesis: DPP-IV inhibition may be useful for the treatment or prevention of hematopoiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6$ M$^{-1}$s$^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-IV have an anxiolytic phenotype (WO 02/34243; Karl et al., *Physiol. Behav.* 2003). DPP-IV deficient mice also have an anxiolytic phenotype using the porsolt and light/dark models. Thus DPP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-IV inhibitors are expected to show similar effects Myocardial Infarction: GLP-1 has been shown to be beneficial when administered to patients following acute myocardial infarction (Circulation, 109: 962-965 (2004)). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.*, 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (*Eur. J. Clin. Chem. Clin. Biochem.*, 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.* 37: 167-173 (1992)).

Osteoporosis: DPP-IV inhibition may be useful for the treatment or prevention of osteoporosis because GIP receptors are present in osteoblasts.

Stem Cell Transplantation: Inhibition of DPP-IV on donor stem cells has been shown to lead to an enhancement of their bone marrow homing efficiency and engraftment, and an increase in survival in mice (Christopherson, et al., *Science,* 305:1000-1003 (2004)). Thus DPP-IV inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, β3 adrenergic receptor agonists, melanocortin-receptor agonists, in particular melanocortin-4 receptor agonists, ghrelin antagonists, bombesin receptor agonists (such as bombesin receptor subtype-3 agonists), cholecystokinin 1 (CCK-1) receptor agonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidide (P32/98); NVP-DPP-728; vildagliptin (LAF 237); P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. Nos. 6,294,534, 6,350,760, 6,376,509, 6,410,548, 6,458,790, 6,472,398, 5,837,521, 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/093234, WO 03/095474, and WO 03/104761.

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared from intermediates such as those of formula II and III using standard reductive amination conditions followed by deprotection. The preparation of these intermediates is described in the following Schemes.

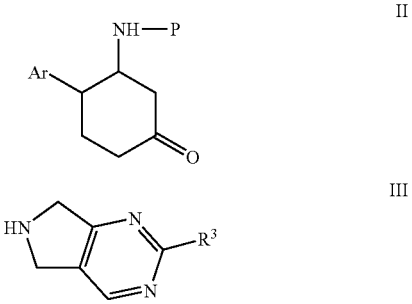

where Ar and $R^3$ are as defined above, and P is a suitable nitrogen protecting group such as tert-butoxycarbonyl (BOC), benzyloxycarbonyl (Cbz), and 9-fluorenylmethoxycarbonyl (Fmoc).

SCHEME 1

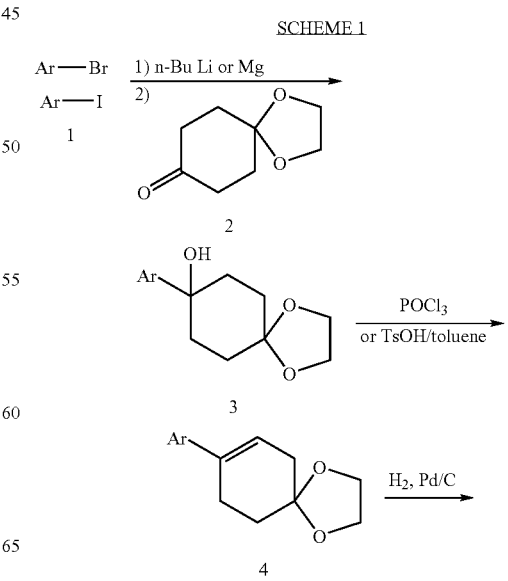

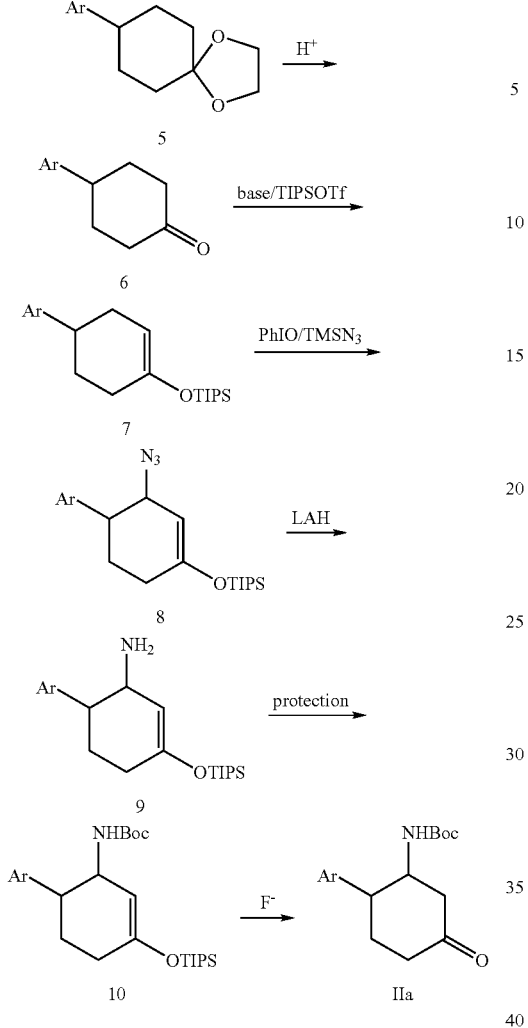

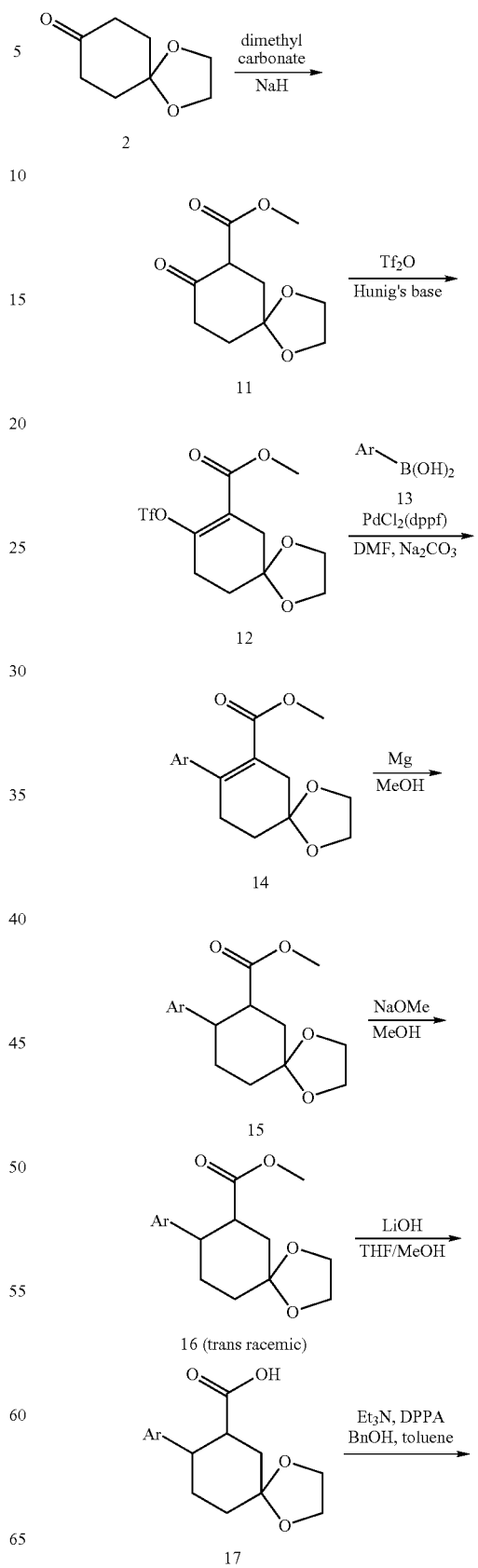

Compounds of formula II are known in the literature or may be conveniently prepared by a variety of methods familiar to those skilled in the art. One common route is illustrated in Scheme 1. An appropriately substituted bromo- or iodobenzene 1 is treated with magnesium to form the corresponding Grignard reagent or lithiated with reagents such as n-butyllithium and then treated with cyclohexanone 2 to form the alcohol 3. Alcohol 3 is dehydrated, for example by treatment with phosphorus oxychloride or by treatment with p-toluenesulfonic acid in toluene with azeotropic removal of water, to provide styrene 4. Reduction by treatment with hydrogen in the presence of a catalyst such as palladium on carbon yields the 4-aryl substituted cyclohexane 5. Deprotection under acidic conditions gives the cyclohexanone 6, which is then converted to a silyl enol ether such as triisopropyl silyl enol ether 7 using reagents and methods familiar to those skilled in the art. The enol ether 7 upon treatment with iodosobenzene and trimethylsilyl azide forms the azido cyclohexene 8, which upon reduction to the amine with lithium aluminum hydride or other reducing agents known in the literature yields the amine 9 as a mixture of cis and trans isomers. Protection of the resulting amine, for example as its BOC derivative by treatment with di-tert-butyl dicarbonate, gives 10. Treatment of 10 with a source of fluoride anion removes the silyl group and gives Intermediate IIa.

-continued

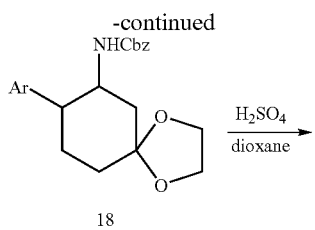

20, which upon treatment and heating with dimethylformamide dimethyl acetal gives 21. The desired intermediate III may then be readily made by heating a solution of 21 with amidine 22 in solvents such as ethanol with or without addition of a base such as sodium ethoxide. Related chemistry is described in international patent publication WO 2003/000657 (3 Jan. 2003).

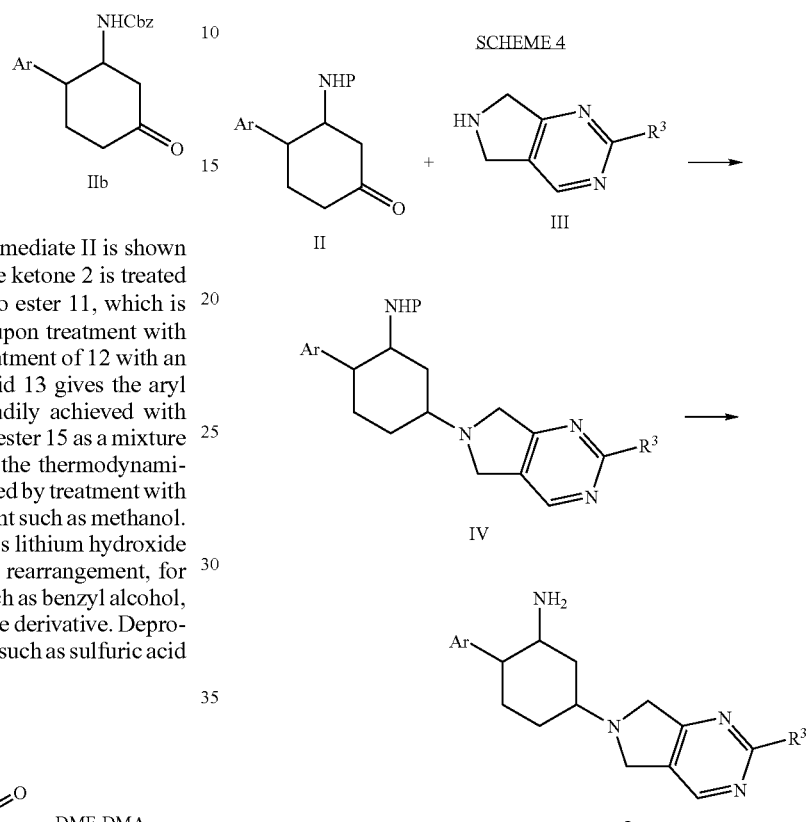

An alternative method to prepare Intermediate II is shown in Scheme 2. The commercially available ketone 2 is treated with dimethyl carbonate to form the keto ester 11, which is then transformed to the enol triflate 12 upon treatment with trifluoromethanesulfonic anhydride. Treatment of 12 with an appropriately substituted arylboronic acid 13 gives the aryl cyclohexene 14. Reduction of 14 is readily achieved with reagents such Mg in methanol to provide ester 15 as a mixture of cis and trans isomers. Conversion to the thermodynamically more stable trans isomer 16 is effected by treatment with a base such as sodium methoxide in solvent such as methanol. Hydrolysis of the ester with a base such as lithium hydroxide to form the acid 17 followed by Curtius rearrangement, for example, in the presence of an alcohol such as benzyl alcohol, gives the amine 18, as its benzylcarbamate derivative. Deprotection of the ketal by treatment with acid such as sulfuric acid in dioxane provides Intermediate IIb.

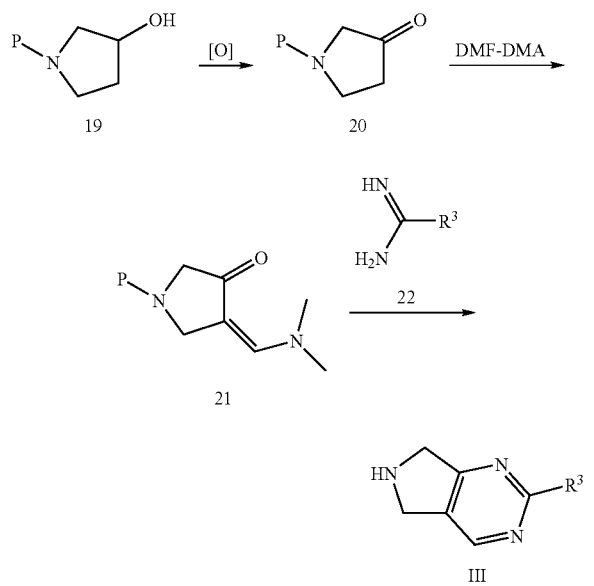

Compounds of formula III are known in the literature or may be conveniently prepared by a variety of methods familiar to those skilled in the art. One common route is illustrated in Scheme 3. Trityl or Boc protected pyrrolidinol 19 may be oxidized by a variety of methods, such as the Swern procedure, commonly known to those in the art to give the ketone As illustrated in Scheme 4, the compounds of the present invention I wherein X is a 6,7-dihydro-5H-pyrrolo[3,4-d]pyrimidine may be made by reductive amination of Intermediate II in the presence of amine III using reagents such as sodium cyanoborohydride, decaborane or sodium triacetoxyborohydride in solvents such as dichloromethane, tetrahydrofuran or methanol to provide intermediate IV. The reaction is conducted with or without a Lewis acid such as titanium tetrachloride or titanium tetraisopropoxide. The reaction may also be facilitated by adding an acid such as acetic acid. In some cases, Intermediate III may be a salt, such as a hydrochloride or trifluoroacetic acid salt, and in these cases it is convenient to add a base, generally N,N-diisopropylethylamine (Hunig's base), to the reaction mixture. The protecting group is then removed with, for example, trifluoroacetic acid or methanolic hydrogen chloride in the case of Boc, or palladium on carbon and hydrogen gas or trimethylsilyl iodide in the case of Cbz to give the desired amine I. The product is purified, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

SCHEME 5

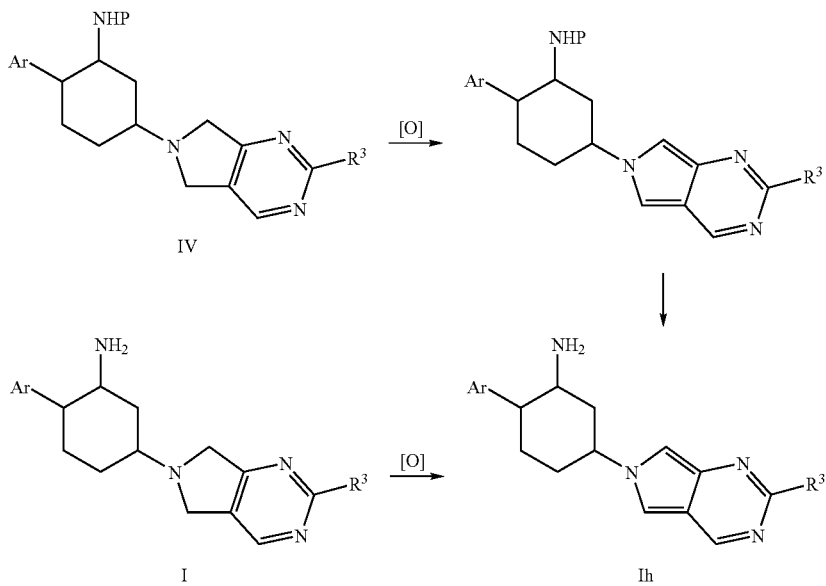

As illustrated in Scheme 5, the compounds of formula Ih wherein X is a 6H-pyrrolo[3,4-d]pyrimidine are made by exposing a solution of intermediate IV or compound I wherein X is a 6,7-dihydro-5H-pyrrolo[3,4-d]pyrimidine to air with or without reagents such as palladium on carbon or by treatment with 2,3-dichloro-5,6-dicyano-1,4-benzoquinone (DDQ). In the case of intermediate IV, removal of the protecting group as described in the previous examples provides compound I.

In some cases the compounds of formula I or synthetic intermediates illustrated in the above schemes may be further modified, for example, by manipulation of substituents on Ar or X. These manipulations may include, but are not limited to, reduction, oxidation, alkylation, acylation, and hydrolysis reactions that are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1 tert-Butyl [(1S,2R)-5-oxo-2-(2,4,5-trifluorophenyl)cyclohexyl]carbamate

Step A: 8-(2,4,5-Trifluorophenyl)-1,4-dioxaspiro[4.5]decan-8-ol

A three neck flask (2 L) under an atmosphere of nitrogen with Mg turnings (9.8 g) was stirred for 15 min and tetrahydrofuran (90 mL) was added and stirring continued for an additional 15 min. 1-Bromo-2,4,5-trifluorobenzene (85 g) was dissolved in tetrahydrofuran (340 mL). A portion of this solution (75 mL) was added to the stirred magnesium turnings and then heated to 50° C. The rest of the solution was added and stirring continued at the same temperature for an additional 1 h. The reaction mixture was cooled to 40° C., a solution of 1,4-dioxaspiro[4.5]decan-8-one (57.3 g) in tetrahydrofuran (275 mL) was added, and stirring continued for 10 h. The reaction mixture was poured into saturated aqueous ammonium chloride solution (970 mL) and extracted with toluene (700 mL). The organic layer was washed with water (3×700 mL), dried over anhydrous sodium sulfate, filtered and evaporated to yield the title compound as a red-orange oil which was used in the next step without further purification.

Step B: 8-(2,4,5-Trifluorophenyl)-1,4-dioxaspiro[4.5]dec-7-ene

To a round-bottomed flask (3 L) under nitrogen atmosphere equipped with a Dean-Stark trap, toluene (350 mL), para-toluenesulfonic acid monohydrate (p-TSA) (1 g) and 8-(2,4,5-trifluorophenyl)-1,4-dioxaspiro[4.5]decan-8-ol (94.2 g) were added and the mixture was refluxed overnight. Additional p-TSA (1 g) was added. Refluxing was continued overnight and then the reaction was stirred at room temperature for two more days. The reaction mixture was treated with 0.1N aqueous sodium hydroxide solution (500 mL) and extracted with heptanes (500 mL). The organic layer was washed with water (3×500 mL), dried over anhydrous sodium sulfate, filtered and evaporated to yield crude product which was purified by column chromatography (silica gel, gradient 2% to 40% ethyl acetate in heptanes) to yield the title compound.

Step C: 8-(2,4,5-Trifluorophenyl)-1,4-dioxaspiro[4.5]decane

A solution of 8-(2,4,5-trifluorophenyl)-1,4-dioxaspiro[4.5]dec-7-ene in methanol (240 mL) and ethyl acetate (5 mL) was treated with 10% palladium on carbon (7.0 g) and stirred under an atmosphere of hydrogen gas (40 psig) overnight. The reaction mixture was filtered over Celite. The filtrate was concentrated and chromatographed (silica gel, gradient 5-7% ethyl acetate in hexane) to yield the title compound.

Step D: 4-(2,4,5-Trifluorophenyl)cyclohexanone 8-(2,4,5-Trifluorophenyl)-1,4-dioxaspiro[4.5]decane (19 g) was added to a solution of 1,4-dioxane (600 mL), water (160 mL) and concentrated sulfuric acid (160 mL) and the resultant mixture was stirred for one h. The solution was then mixed with water (1 L) and extracted with dichloromethane (1 L). The organic layer was washed with water, dried over anhydrous magnesium sulfate filtered and evaporated to yield the title compound as a white solid.

Step E: Triisopropyl{[4-(2,4,5-trifluorophenyl)cyclohex-1-en-1-yl]oxy}silane

A three-neck flask (1 L) containing a stirred solution of 4-(2,4,5-trifluorophenyl)cyclohexanone (15.8 g) in dichloromethane (160 mL) under a nitrogen atmosphere was cooled to 0° C. and then treated with triethylamine (22 mL) followed by triisopropylsilyl trifluoromethanesulfonate (25.4 g) while maintaining the temperature below 5° C. The solution was stirred at 0° for 30 min and then allowed to rise to ambient temperature over a period of 0.5 h. It was then treated with saturated aqueous ammonium chloride solution. The organic layer was separated, dried over anhydrous magnesium sulfate and evaporated. The crude product was chromatographed (silica gel, 3% ether in hexane) to yield the title compound.

Step F: {[3-Azido-4-(2,4,5-trifluorophenyl)cyclohex-1-en-1-yl]oxy}(triisopropyl)silane In a three-neck flask, a stirred solution of triisopropyl {[4-(2,4,5-trifluorophenyl)cyclohex-1-en-1-yl]oxy}silane (26.06 g, 0.068 mol) in dichloromethane (260 mL) was cooled to −15° C. and treated with iodosobenzene (19.5 g, 0.089 mol) in four portions followed by azidotrimethylsilane (24 mL, 0.116 mol) while maintaining the temperature below −10° C. Stirring was continued for 1.5 h. The reaction mixture was allowed to warm to room temperature briefly, then cooled again back to −15° C. and filtered. The filtrate was evaporated under vacuum below 25° C. to give the title compound which was used directly in the next step.

Step G: trans 6-(2,4,5-Trifluorophenyl)-3-[(triisopropylsilyl)oxy]cyclohex-2-en-1-amine To a stirred solution of {[3-azido-4-(2,4,5-trifluorophenyl)cyclohex-1-en-1-yl]oxy}(triisopropyl)silane (48.2 g) in ether (280 mL) at 0° C. in a three-neck flask (1 L) was added lithium aluminum hydride (1M in ether, 85 mL) while maintaining the temperature below 5° C. The reaction mixture was allowed to warm up to room temperature after completion of addition of the hydride. The mixture was transferred to ice with some saturated aqueous ammonium chloride solution and filtered. The residue was washed with ethyl acetate (1 L), and the organic layer separated, dried over anhydrous sodium sulfate, filtered, and concentrated. The residue was chromatographed (silica gel, gradient 10-35% ethyl acetate in heptane) to yield the faster eluting cis- and the slower-eluting trans 6-(2,4,5-trifluorophenyl)-3-[(triisopropylsilyl)oxy]cyclohex-2-en-1-amine.

Step H: trans tert-Butyl(6-(2,4,5-trifluorophenyl)-3-[(triisopropylsilyl)oxy]cyclohex-2-en-1-yl)carbamate To a round bottomed flask (500 mL) containing trans-6-(2,4,5-trifluorophenyl)-3-[(triisopropylsilyl)oxy]cyclohex-2-en-1-amine (8.77 g) dissolved in dichloromethane (80 mL), triethylamine (3.5 mL) and di-tert-butyl dicarbonate (1.0M in tetrahydrofuran, 25 ml) were added. The mixture was stirred overnight. The next day the solution was evaporated and the concentrated red residue was chromatographed (silica gel, gradient 25-85% dichloromethane-hexane) to yield the desired product.

Step I: tert-Butyl [(1S,2R)5-oxo-2-(2,4,5-trifluorophenyl)cyclohexyl]carbamate

To a round-bottomed flask (500 mL) containing trans tert-butyl(6-(2,4,5-trifluorophenyl)-3-[(triisopropylsilyl)oxy]cyclohex-2-en-1-yl)carbamate (10.7 g) dissolved in tetrahydrofuran (100 mL), tetrabutylammonium fluoride (1M in tetrahydrofuran, 26 mL) was added and the mixture was stirred for 1 h. The solution was concentrated to a dark brown oil and purified by chromatography (silica gel, gradient 20%-40% ethyl acetate in hexane) to yield the product as a mixture of enantiomers. HPLC using a chiral AD column (12% isopropanol in heptane) gave the title compound as the slower eluting isomer. LC/MS 227.1 (M+1).

INTERMEDIATE 2

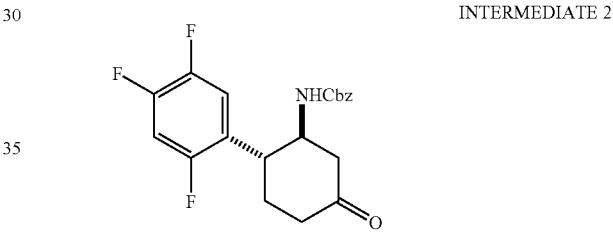

Benzyl [(1S,2R)-5-Oxo-2-(2,4,5-trifluorophenyl)cyclohexyl]carbamate

Step A: Methyl 8-oxo-1,4-dioxaspiro[4.5]decane-7-carboxylate

To a stirred solution of 1,4-cyclohexanedione monoethylene ketal (1.00 g, 6.4 mmol) in dimethyl carbonate (6 mL) at room temperature was added sodium hydride (0.31 g, 7.7 mmol). The mixture was heated at 80° C. for 20 min and then diluted with dry toluene (20 mL). The mixture was stirred for an additional 3 h at 80° C., cooled to room temperature, quenched with water, and then extracted with dichloromethane. The organic phase was dried over anhydrous sodium sulfate and evaporated to yield the crude product which was purified by Biotage® chromatography (silica gel, ethyl acetate in hexanes gradient 30-42%) to yield the title compound.

Step B: 7-(Methoxycarbonyl)-8-{[(trifluoromethyl)sulfonyl]oxy}-4-oxa-1-oxoniaspiro[4.5]dec-7-ene To a stirred solution of methyl 8-oxo-1,4-dioxaspiro[4.5]decane-7-carboxylate (2.14 g, 10 mmol) in dichloromethane (22 mL) at −78° C. was added N,N-diisopropylethylamine (8.5 mL, 48.8 mmol). After 10 min, trifluoromethanesulfonic anhydride (2.0 mL, 12 mmol) was added dropwise. The resulting mixture was stirred overnight while the temperature was allowed to warn up to room temperature. The mixture was diluted with ethyl acetate and washed with 10% aqueous citric acid solution. The organic phase was dried over anhydrous sodium sulfate and evaporated to yield the title compound.

Step C: Methyl 8-(2,4,5-trifluorophenyl)-1,4-dioxaspiro[4.5]dec-7-ene-7-carboxylate To a stirred solution of 7-(methoxycarbonyl)-8-{[(trifluoromethyl)sulfonyl]oxy}-4-oxa-1-oxoniaspiro[4.5]dec-7-ene (5.65 g, 16.0 mmol) dissolved in N,N-dimethylformamide (190 mL) were added aqueous sodium carbonate solution (2.0M, 20 mL, 39.0 mmol) and 2,4,5-trifluorophenylboronic acid (4.11 g, 23.4 mmol). The resulting mixture was degassed and treated with PdCl$_2$(dppf) ([1,1'-bis(diphenylphosphino)-ferrocene]dichloropalladium(II), complex with dichloromethane (1:1), 1274 mg). The resulting mixture was stirred under a nitrogen atmosphere at room temperature overnight, filtered over Celite, diluted with ethyl acetate and washed with water. The organic phase was dried over anhydrous sodium sulfate, evaporated and the crude product was purified by chromatography on a Biotage® system (silica gel, ethyl acetate in hexanes gradient 30-50%) to yield the title compound.

Step D: Methyl 8-(2,4,5-trifluorophenyl)-1,4-dioxaspiro[4.5]decane-7-carboxylate To a stirred solution of methyl 8-(2,4,5-trifluorophenyl)-1,4-dioxaspiro[4.5]dec-7-ene-7-carboxylate (1.93 g, 5.9 mmol) in methanol (50 mL) was added magnesium (1.43 g, 59 mmol), and the mixture was refluxed overnight under nitrogen atmosphere. The white precipitate that formed was filtered over Celite, and the filtrate was evaporated under reduced pressure to yield the title compound.

Step E: trans Methyl 8-(2,4,5-trifluorophenyl)-1,4-dioxaspiro[4.5]decane-7-carboxylate To a stirred solution of 8-(2,4,5-trifluorophenyl)-1,4-dioxaspiro[4.5]decane-7-carboxylate (1.95 g, 5.9 mmol) in methanol (50 mL) was added sodium methoxide (0.5M in methanol, 14.2 ml, 7.1 mmol), and the resulting solution was refluxed overnight under a nitrogen atmosphere, cooled to room temperature and evaporated to yield the crude product which was purified by chromatography on a Biotage® system (silica gel, ethyl acetate in hexanes gradient 25-54%) to yield the title compound containing some cis isomer.

Step F: trans 8-(2,4,5-Trifluorophenyl)-1,4-dioxaspiro[4.5]decane-7-carboxylic acid A stirred solution of trans 8-(2,4,5-trifluorophenyl)-1,4-dioxaspiro[4.5]decane-7-carboxylate from Step E (1.82 g, 5.5 mmol) dissolved in tetrahydrofuran (11 mL) and methanol (22 mL) was treated with aqueous lithium hydroxide solution (1.0M, 18.5 mL) and the mixture was stirred at room temperature overnight. The reaction solution was acidified with hydrochloric acid (1N) to pH 1 and extracted with ethyl acetate. The organic phase was washed by saturated brine solution, dried over anhydrous sodium sulfate and evaporated to yield the title compound.

Step G: Benzyl [8-(2,4,5-trifluorophenyl)-1,4-dioxaspiro[4,5]dec-7-yl]carbamate

A stirred solution of trans 8-(2,4,5-trifluorophenyl)-1,4-dioxaspiro[4.5]decane-7-carboxylic acid (500 mg, 1.29 mmol) in toluene (20 mL) was treated with diphenylphosphoryl azide (0.33 mL, 1.55 mmol), triethylamine (0.22 mL, 1.55 mmol) and anhydrous benzyl alcohol (0.33 mL, 3.2 mmol) at room temperature under a nitrogen atmosphere. After heating at 90° C. for 2 days, the reaction mixture was evaporated under reduced pressure and the residue was diluted with ethyl acetate and washed with saturated aqueous sodium bicarbonate solution. The organic phase was dried over anhydrous sodium sulfate and evaporated to yield the crude product which was purified by chromatography on a Biotage® system (silica gel, ethyl acetate in hexanes gradient 25-40%) to yield the title compound.

Step H: Benzyl [(7S,8R)-8-(2,415-trifluorophenyl)-1,4-dioxaspiro[4.5]dec-7-yl]carbamate Benzyl [8-(2,4,5-trifluorophenyl)-1,4-dioxaspiro[4.5]dec-7-yl]carbamate (528 mg) was resolved by HPLC using a chiral AD column (13% isopropanol in heptane) to give benzyl [(7S,8R)-8-(2,4,5-trifluorophenyl)-1,4-dioxaspiro[4.5]dec-7-yl]carbamate as the slower eluting enantiomer.

Step I: Benzyl [(1S,2R)-5-oxo-2-(2,4,5-trifluorophenyl)cyclohexyl]carbamate

To a stirred solution of benzyl [(7S,8R)-8-(2,4,5-trifluorophenyl)-1,4-dioxaspiro[4.5]dec-7-yl]carbamate (315 mg, 0.75 mmol) in sulfuric acid (15 mL, 1:1 in water) was added 1,4-dioxane (30 mL). The mixture was stirred at room temperature for 1 h. The resulting mixture was poured into water (70 mL) and extracted with dichloromethane. The organic layer was dried over anhydrous sodium sulfate and evaporated to yield the title compound. LC/MS 378.0 (M+1).

INTERMEDIATE 3

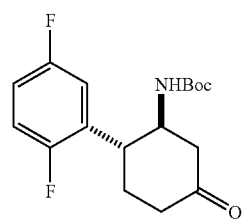

tert-Butyl [(1S,2R)-5-oxo-2-(2,5-difluorophenyl)cyclohexyl]carbamate

The title compound was prepared from 1-bromo-2,5-difluorobenzene generally following the procedures outlined for the synthesis of Intermediate 1. LC/MS 209.1 (M+1).

INTERMEDIATE 4

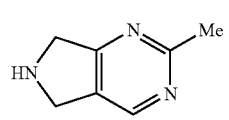

2-Methyl-6,7-dihydro-5H-pyrrolo[3,4-d]pyridine

Step A: 1-Tritylpyrrolidin-3-one

To a stirred solution of anhydrous dichloromethane (35.0 mL) in a 3-necked flask with a thermometer, oxalyl chloride (1.5 mL) was added and the resulting solution was cooled to −60° C. A solution of dimethyl sulfoxide (2.6 mL) in dichloromethane (7.5 mL) was added over a period of 10 min, and then (3R)-1-tritylpyrrolidin-3-ol (5.0 g) in dichloromethane (15.0 mL) was added over a period of 10 min. The resulting solution was stirred at −60° C. for 15 min., then triethylamine (10.6 mL) was added over a period of 5 min. A white precipitate was formed. After 5 rain, the cooling bath was removed and the mixture was allowed to warm to room temperature. Water (45 mL) was added. The mixture was stirred for an additional 30 min and then extracted with dichloromethane. The organic phase was washed with 5% aqueous citric acid solution, dried over anhydrous sodium sulfate, filtered and concentrated to yield the title compound. LC-MS=243.1 (M+1).

Step B: 4-[(Dimethylamino)methylene]-1-tritylpyrrolidin-3-one

A suspension of 1-tritylpyrrolidin-3-one (4.9 g) from Step A in anhydrous DMF (36.0 mL) was dissolved by heating at 80° C. under nitrogen for 10 min. The clear solution was treated with N,N-dimethylformamide dimethyl acetal (18.0 mL) and heated at 80° C. for 12 h. The resulting dark brown solution was evaporated under reduced pressure. The residue was chromatographed on a Biotage® system (silica gel, gradient from 50% to 100% ethyl acetate in hexanes) to yield the title compound. LC-MS=243.1 (M+1).

Step C: 2-Methyl-6,7-dihydro-5H-pyrrolo[3,4-d]pyrimidine

A solution of acetamidine hydrochloride (12.8 g, 135 mmol) and sodium ethoxide (59 mL, 157.5 mmol) in anhydrous ethanol (400 mL) was stirred under nitrogen for 15 min, and 4-[(dimethylamino)methylene]-1-tritylpyrrolidin-3-one from Step B (17.2 g, 45 mmol) was added. The resulting mixture was heated at 85° C. for 3.5 h, quenched with a solution of 5% aqueous citric acid (50 mL), and evaporated to dryness. The residue was dissolved in ethyl acetate (500 mL) and washed with saturated aqueous sodium bicarbonate solution. There was some insoluble solid material between the aqueous and the organic layers, which was filtered thorough a Celite pad and washed with ethyl acetate. The combined aqueous layers were extracted twice with ethyl acetate. The organic layers were combined and washed with saturated aqueous sodium bicarbonate solution and brine, dried over anhydrous sodium sulfate, and concentrated. The residue obtained was purified by chromatography on a Biotage Horizon® system (silica gel, 0-75% ethyl acetate/dichloromethane gradient) to yield the N-trityl protected derivative of the desired product. A portion of this trityl protected product (1.9 g, 5.0 mmol) was dissolved in 4N methanolic hydrogen chloride (20 mL) and stirred at room temperature for 2.5 h. The solution was evaporated and the residue was purified by chromatography on a Biotage Horizon® system (silica, 4.5-14% gradient of 10% concentrated aqueous ammonium hydroxide in methanol/dichloromethane) to yield the desired product. LC-MS=136.0 (M+1).

INTERMEDIATE 5

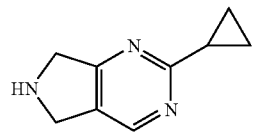

2-Cyclopropyl-6,7-dihydro-5H-pyrrolo[3,4-d]pyrimidine

2-Cyclopropyl-6,7-dihydro-5H-pyrrolo[3,4-d]pyrimidine was made from cyclopropylcarbamidine hydrochloride (16.28 g, 135 mmol) and 4-[(dimethylamino)methylene]-1-tritylpyrrolidin-3-on (17.2 g, 45 mmol) by essentially following the method described in Step C of Intermediate 4 to yield the desired product. LC-MS=162.1 (M+1).

INTERMEDIATE 6

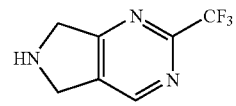

2-(Trifluoromethyl)-6,7-dihydro-5H-pyrrolo[3,4-d]pyrimidine

Step A: tert-Butyl 3-[(dimethylamino)methylene]-4-oxopyrrolidine-1-carboxylate

A solution of 1-(tert-butoxylcarbonyl)-3-pyrrolidone (4.10 g) and N,N-dimethylformamide dimethyl acetal (30.0 mL) was heated to 140° C. for 1 h. The resulting mixture was cooled to room temperature and concentrated under reduced pressure. The residue was redissolved in a minimum amount of dichloromethane and triturated with hexane to yield a yellow precipitate. LC-MS 241.1 (M+1).

Step B: 2-(Trifluoromethyl)-6,7-dihydro-5H-pyrrolo[3,4-d]pyrimidine

To a solution of the product from Step A (500 mg) in anhydrous ethanol (25 mL) was added sodium ethoxide (2.33 mL, 21% in ethanol). After stirring for 5 min, trifluoroacetamidine (700 mg) was added and the resulting mixture was heated to reflux for 1 h. The reaction mixture was cooled to room temperature and diluted with ethyl acetate. The organic layer was washed sequentially with 5% aqueous citric acid solution and brine, dried over anhydrous sodium sulfate, filtered and concentrated to give a crude product which was deprotected by dissolving in 1N methanolic hydrogen chloride for 1 h. The resulting solution was concentrated and chromatographed on a Biotage® system (silica gel cartridge, gradient from 10% to 18% of 10% concentrated aqueous ammonium hydroxide in methanol/dichloromethane) to yield the title compound. LC-MS=190.0 (M+1).

INTERMEDIATE 7

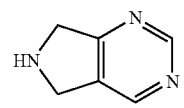

6,7-Dihydro-5H-pyrrolo[3,4-d]pyrimidine

To a solution of formamidine hydrochloride (190 mg) in anhydrous ethanol (25.0 mL) under nitrogen were added sodium ethoxide (21% wt in ethanol, 1.2 mL) and 4-[(dimethylamino)methylene]-1-tritylpyrrolidin-3-one (300 mg, prepared as described for Step B, Intermediate 4). The mixture was refluxed at 80° C. for 8 h. The reaction mixture was cooled to ambient temperature and diluted with ethyl acetate. The organic layer was washed sequentially with 5% aqueous citric acid solution and brine, dried over anhydrous sodium sulfate, filtered, concentrated. The crude residue was deprotected by treatment with 4N methanolic hydrogen chloride for 2.5 h. The mixture was concentrated and the residue purified by chromatography on a Biotage® system (silica, gradient 15% to 25% of 10% concentrated ammonium hydroxide in methanol/dichloromethane) to give the title compound. LC-MS=243.1 (M+1).

INTERMEDIATE 8

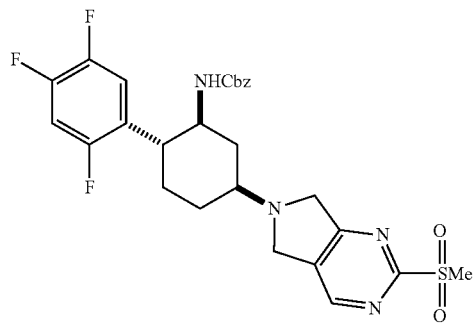

Benzyl [(1S,2R,5S)-5-[2-(methylsulfonyl)-5,7-dihydro-6H-pyrrolo[3,4-d]pyridin-6-yl]-2-(2,4,5-trifluorophenyl)cyclohexyl]carbamate Step A: 2-(Methylthio)-6-trityl-6,7-dihydro-5H-pyrrolo[3,4-d]pyrimidine To a solution of 4.83 g (12.63 mmol) of 4-[(dimethylamino)methylene]-1-tritylpyrrolidin-3-one in anhydrous ethanol (50 mL) was added sodium ethoxide (11.8 mL, 21% in ethanol). After stirring for 5 min, 3.51 g (25.25 mmol) of 2-methyl-2-thiopseudourea sulfate was aided and the reaction mixture heated at reflux temperature for 1 h. The mixture was cooled to ambient temperature and 3.51 g (25.25 mmol) of 2-methyl-2-thiopseudourea sulfate was added followed by 11.8 mL (21% in ethanol) of sodium ethoxide. The reaction mixture was refluxed for 1 h and cooled to ambient temperature. This process was repeated two additional times at which point the reaction mixture was evaporated in vacuo, diluted with 200 mL of a 1:1 mixture of ethyl acetate and saturated aqueous brine. The layers were separated and the aqueous phase extracted with three 100-mL portions of ethyl acetate. The combined organic phase was dried over magnesium sulfate, filtered and evaporated in vacuo. The resulting residue was chromatographed on a Biotage® system (silica gel, 0 to 25% ethyl acetate/hexanes gradient) to yield the title compound as a white solid. LC/MS=410.3 (M+1).

Step B: 2-(Methylthio)-6,7-dihydro-5H-pyrrolo[3,4-d]pyrimidine

To 1.5 g of the product from Step A was added 15 mL (4.0 M in 1,4-dioxane) of hydrochloric acid and the solution stirred for 1 h and then concentrated in vacuo. The crude residue was chromatographed on a Biotage® system (silica gel, 0 to 50% methanol/ethyl acetate, 1% ammonium hydroxide) to give the title compound as a white solid. LC/MS 167.3 (M+1).

Step C: Benzyl [(1S,2R,1S)-5-[2-(methylthio)-5,7-dihydro-6H-pyrrolo[3,4-d]pyrimidin-6-yl]-2-(2,4,5-trifluorophenyl)cyclohexyl]carbamate To a solution of 717 mg (1.9 mmol) of Intermediate 2 and 318 mg (1.9 mmol) of the product from Step B in 13 mL of methanol was added 77 mg (0.63 mmol) of decaborane. The reaction mixture was stirred for 18 h, concentrated in vacuo, and the residue chromatographed on a Biotage® system (silica gel, 0 to 70% hexanes/ethyl acetate) to give the title compound as a white solid. LC/MS 529.3 (M+1).

Step D: Benzyl [(1S,2R,5S)-5-[2-(methylsulfonyl)-5,7-dihydro-6H-pyrrolo[3,4-d]pyrimidin-6-yl]-2-(2,4,5-trifluorophenyl)cyclohexyl]carbamate To a solution of 112 mg (0.21 mmol) of the product from Step C in 4 mL of a 1:1 mixture of ethyl acetate and isopropanol was added 0.8 mL (4.0 M in 1,4-dioxane) of anhydrous hydrochloric acid. After stirring for 10 min, 0.3 mL (30% in water) hydrogen peroxide was added and the reaction mixture stirred for 2 h. The reaction mixture was diluted with 15 mL of diethyl ether and poured into 22 mL of an ice-cold mixture of 1:5:5 of saturated aqueous sodium thiosulfite/saturated aqueous sodium bicarbonate/saturated aqueous brine. The layers were separated and the aqueous phase extracted with three 5-mL portions of diethyl ether. The combined organic phases were dried over magnesium sulfate, filtered and concentrated in vacuo and used without further purification. LC/MS 561.1 (M+1).

INTERMEDIATE 9

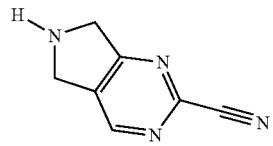

6,7-Dihydro-5H-pyrrolo[3,4-d]pyrimidine-2-carbonitrile

Step A: tert-Butyl 3-[(dimethylamino)methylene]-4-oxopyrrolidine-1-carboxylate

A solution of 1-(tert-butoxylcarbonyl)-3-pyrrolidone (4.10 g) and N,N-dimethylformamide dimethyl acetal (30.0 mL) was heated to 140° C. for 1 h. The resulting mixture was cooled to room temperature and concentrated under reduced pressure. The residue was redissolved in a minimum amount of dichloromethane and triturated with hexane to yield the desired product as a yellow precipitate. LC-MS=241.1 (M+1).

Step B: tert-Butyl 2-(methylthio)-5,7-dihydro-6H-pyrrolo[3,4-d]pyrimidine-6-carboxylate To a solution of 2-methyl-2-thiopseudourea sulfate (3.5 g, 25 mmol) in ethanol at 0° C. was added a solution of sodium ethoxide (9.6 mL, 21%). After stirring for 10 min, a solution of tert-butyl 3-[(dimethylamino)methylene]-4-oxopyrrolidine-1-carboxylate (2.0 g, 8.32 mmol) in ethanol was added, and the mixture was heated at 80° C. for 1 h. Additional 2-methyl-2-thiopseudourea sulfate (3.5 g, 25 mmol) and sodium ethoxide (9.6 mL, 21%) was added and heated at 80° C. for 1 h. The ethanol was removed under reduced pressure, the residue was diluted with ethyl acetate (400 mL), washed with saturated aqueous sodium bicarbonate, brine, dried over sodium sulfate, and concentrated. The residue was purified on a Biotage silica gel cartridge (gradient 10-35% ethyl acetate in hexanes) to yield tert-butyl 2-(methylthio)-5,7-dihydro-6H-pyrrolo[3,4-d]pyrimidine-6-carboxylate.

Step C: tert-Butyl 2-(methylsulfonyl)-5,7-dihydro-6H-pyrrolo[3,4-d]pyrimidine-6-carboxylate To a solution of tert-butyl 2-(methylthio)-5,7-dihydro-6H-pyrrolo[3,4-d]pyrimidine-6-carboxylate (868 mg, 3.25 mmol) in anhydrous dichloromethane (16 mL) at 0° C., 3-chloroperoxybenzoic acid (2.67 g, 60%, 9.28 mmol) was added. The resulting mixture was stirred at 0° C. for 5 h. The ice bath was then removed, the crude product was diluted with dichloromethane and washed with saturated aqueous sodium bicarbonate solution. The organic phase was dried over sodium sulfate and concentrated to yield the desired product. LC-MS=300.2 (M+1).

Step D: tert-Butyl 2-cyano-5,7-dihydro-6H-pyrrolo[3,4-d]pyrimidine-6-carboxylate To a solution of the methylsulfone from Step C (1.2 g, 4.0 mmol) in dichloromethane was added tetrabutylammonium cyanide (1.13 g, 4.2 mmol). The resulting mixture was stirred at room temperature overnight. It was then diluted with dichloromethane (100 mL) and 1N sodium hydroxide (100 mL). The aqueous layer was extracted with ethyl acetate (200 mL), and the combined organic layers were washed with brine, dried over sodium sulfate, and concentrated. The residue was purified on a Biotage silica gel cartridge (gradient 35-55% ethyl acetate in hexanes) to yield tert-butyl 2-cyano-5,7-dihydro-6H-pyrrolo[3,4-d]pyrimidine-6-carboxylate.

Step E: 6,7-Dihydro-5H-pyrrolo[3,4-d]pyrimidine-2-carbonitrile

A solution of tert-butyl 2-cyano-5,7-dihydro-6H-pyrrolo[3,4-d]pyrimidine-6-carboxylate (150 mg) in trifluoroacetic acid and dichloromethane (1:1, 1 mL) was stirred for one h and evaporated. The residue was purified by flash column chromatography (silica, 0-4% methanol containing 10% ammonium hydroxide in dichloromethane) to yield 6,7-dihydro-5H-pyrrolo[3,4-d]pyrimidine-2-carbonitrile.

INTERMEDIATE 10

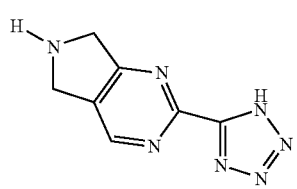

2-(1H-Tetrazol-5-yl)-6,7-dihydro-5H-pyrrolo[3,4-d]pyrimidine

To a solution of tert-butyl 2-cyano-5,7-dihydro-6H-pyrrolo[3,4-d]pyrimidine-6-carboxylate (Intermediate 9, Step D) (71 mg, 0.29 mmol) in toluene was added azidotrimethyltin (596 mg, 2.9 mmol). The resulting mixture was heated at 110° C. overnight. After the solvent was removed under reduced pressure, the residue was purified by reverse-phase silica gel chromatography (gradient 5-50% acetonitrile in water containing 0.1% TFA) to yield tert-butyl 2-(1H-tetrazol-5-yl)-5,7-dihydro-6H-pyrrolo[3,4-d]pyrimidine-6-carboxylate. The product was treated as described for Intermediate 9, Step E, to yield the title compound.

INTERMEDIATE 11

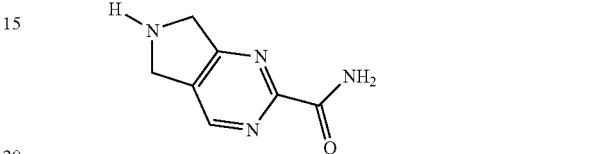

6,7-Dihydro-5H-pyrrolo[3,4-d]pyrimidine-2-carboxamide

A solution of tert-butyl 2-cyano-5,7-dihydro-6H-pyrrolo[3,4-d]pyrimidine-6-carboxylate (Intermediate 9, Step D) (190 mg, 0.77 mmol) in 4.8N of hydrogen chloride (3 mL) was heated at 80° C. for 2 h. After the solvent was removed under reduced pressure, the residue was purified by prep-TLC, eluting with 13% methanol containing 1N of ammonia in dichloromethane to yield tert-butyl 2-(aminocarbonyl)-5,7-dihydro-6H-pyrrolo[3,4-d]pyrimidine-6-carboxylate. The product was treated as described for Intermediate 9, Step E, to yield the title compound.

INTERMEDIATE 12

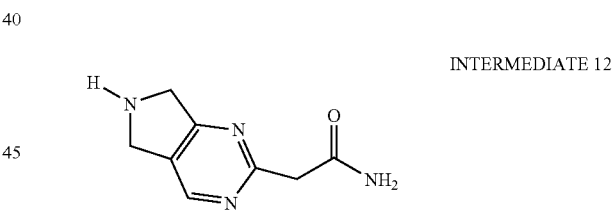

2-(6,7-Dihydro-5H-pyrrolo[3,4-d]pyrimidin-2-yl)acetamide

To a suspension of malonamamidine hydrogen chloride (773 mg, 5.6 mmol) in ethanol at 0° C. was added a solution of sodium ethoxide (2.2 mL, 21%). After stirring for 15 min, a solution of tert-butyl 3-[(dimethylamino)methylene]-4-oxopyrrolidine-1-carboxylate (450 mg, 1.9 mmol) in ethanol was added, and the mixture was heated at 85° C. for 4 h. The ethanol was removed under reduced pressure, the residue was diluted by ethyl acetate (150 mL), washed with saturated aqueous sodium bicarbonate, brine, dried over sodium sulfate, and concentrated. The residue was purified on a Biotage silica gel cartridge (gradient 10-35% ethyl acetate containing 0.1% ethanol and 0.01% ammonia hydroxide in hexanes).

The product was treated as described for Intermediate 9, Step E, to yield the title compound.

EXAMPLE 1

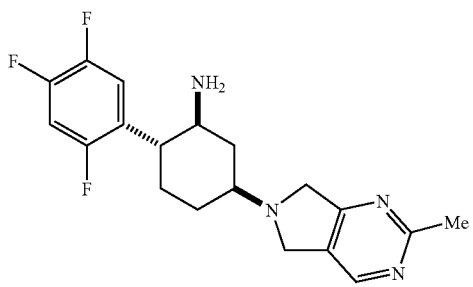

[(1S,2R,5S)-5-[2-Methyl-5,7-dihydro-6H-pyrrolo[3,4-d]pyrimidin-6-yl]-2-(2,4,5-trifluorophenyl)cyclohexyl]amine To a solution of benzyl [(1S,2R)-5-oxo-2-(2,4,5-trifluorophenyl)cyclohexyl]carbamate (Intermediate 2, 800 mg) in anhydrous methanol (20 mL) under nitrogen were added 2-methyl-6,7-dihydro-5H-pyrrolo[3,4-d]pyrimidine (Intermediate 4, 286 mg) and decaborane (77 mg). After stirring at room temperature overnight, the reaction mixture was concentrated and chromatographed on a Biotage Horizon® system (silica gel, 60-80% ethyl acetate/dichloromethane gradient followed by 4-6.5% of 10% concentrated aqueous ammonium hydroxide in methanol/dichloromethane gradient). The slower eluting N-Cbz protected compound (430 mg) was dissolved in methanol (13 mL) and treated with palladium hydroxide on carbon (86 mg) under an atmosphere of hydrogen for 2 h. The mixture was filtered and concentrated, and the residue obtained as such was purified by preparative thin layer chromatography (TLC, silica, 1:11:88 ammonium hydroxide/methanol/dichloromethane) to yield the desired compound. LC-MS=363.1 (M+1).

EXAMPLE 2

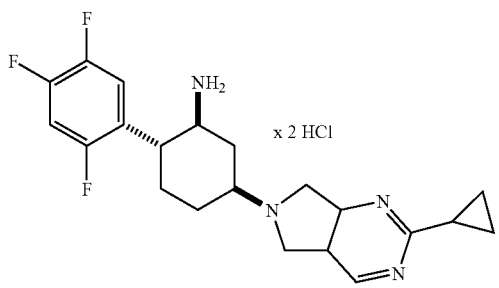

[(1S,2R,5S)-5-[2-Cyclopropyl-5,7-dihydro-6H-pyrrolo[3,4-d]pyrimidin-6-yl]-2-(2,4,5-trifluorophenyl)cyclohexyl]amine, dihydrochloride salt To a solution of tert-butyl [(1S,2R)-5-oxo-2-(2,4,5-trifluorophenyl)cyclohexyl]carbamate (Intermediate 1, 464 mg) in anhydrous methanol (19.0 mL) under nitrogen were added 2-cyclopropyl-6,7-dihydro-5H-pyrrolo[3,4-d]pyrimidine (Intermediate 5, 218 mg) and decaborane (11 mg). After stirring at room temperature overnight, the reaction mixture was concentrated and chromatographed using a Biotage® system (silica gel, 4-8% of 10% concentrated ammonium hydroxide in methanol dichloromethane). The slower eluting desired compound was recovered and deprotected in 1N methanolic hydrogen chloride for 40 min, and concentrated. Purification by preparative TLC (silica, 1:8:91 ammonium hydroxide/methanol/dichloromethane) afforded the title compound.

$^1$H NMR (500 MHz, CD$_3$OD): Key resonances: δ 3.99 (s, 2H), 4.07 (s, 2H), 8.45 (s, 1H).

LC-MS=389.1 (M+1). The free base was converted to its dihydrochloride salt by dissolving it in 1N methanolic hydrogen chloride and evaporating under reduced pressure.

EXAMPLE 3

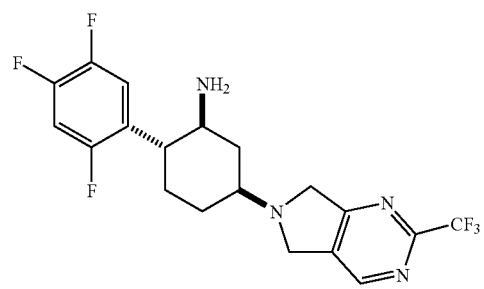

[(1S,2R,5S)-5-[2-(Trifluoromethyl)-5,7-dihydro-6H-pyrrolo[3,4-d]pyrimidin-6-yl]-2-(2,4,5-trifluorophenyl)cyclohexyl]amine Step A: tert-Butyl [(1S,2R,5)-5-[2-(trifluoromethyl)-5,7-dihydro-6-pyrrolo[3,4-d]pyrimidin-6-yl]-2-(2,4,5-trifluorophenyl)cyclohexyl]carbamate To a solution of tert-butyl [(1S,2R)-5-oxo-2-(2,4,5-trifluorophenyl)cyclohexyl]carbamate (Intermediate 1, 100 mg) in anhydrous methanol (4.0 mL) under nitrogen were added 2-(trifluoromethyl)-6,7-dihydro-5H-pyrrolo[3,4-d]pyrimidine (Intermediate 6, 55 mg) and decaborane (11 mg). After stirring at room temperature overnight, the reaction mixture was concentrated and chromatographed by preparative TLC (silica gel, 1:6:93 ammonium hydroxide/methanol/dichloromethane). The slower eluting desired isomer was recovered.

Step B: [(1S,2R,5S)-5-[2-(Trifluoromethyl)-5,7-dihydro-6H-pyrrolo[3,4-d]pyrimidin-6-yl]-2-(2,4,5-trifluorophenyl)cyclohexyl]amine The compound from Step A was dissolved in 4N hydrogen chloride in 1,4-dioxane for 1 h, concentrated and purified by preparative TLC (silica, 1:9:90 ammonium hydroxide/methanol/dichloromethane) to yield the title compound.

$^1$H NMR (500 MHz, CD$_3$OD): Key resonances: δ 4.16 (s, 2H), 4.20 (s, 2H), 8.80 (s, 1H).

LC-MS=363.1 (M+1).

Following essentially the procedures outlined for Examples 1-3, the Examples listed in Table 1 were prepared.

TABLE 1

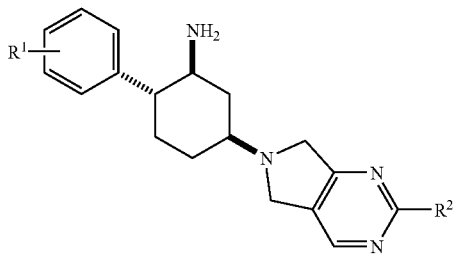

| Example | R[1] | R[2] | MS (M + 1) |
|---|---|---|---|
| 4 | 2-F, 5-F | Me | 345.2 |
| 5 | 2-F, 5-F | cyclopropyl | 371.2 |
| 6 | 2-F, 5-F | $CF_3$ | 399.2 |
| 7 | 2-F, 4-F, 5-F | H | 349.1 |

EXAMPLE 8

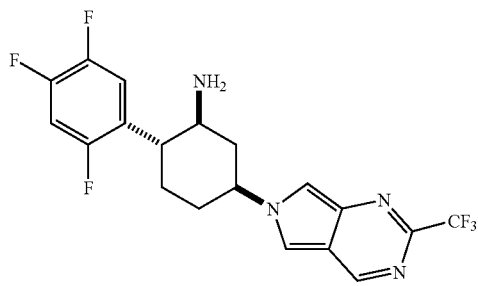

[(1S,2R,5S)-5-[2-(Trifluoromethyl)-6H-pyrrolo[3,4-d]pyrimidin-6-yl]-2-(2,4,5-trifluorophenyl)cyclohexyl]amine A solution of benzyl [(1S,2R,5S)-5-[2-(trifluoromethyl)-5,7-dihydro-6H-pyrrolo[3,4-d]pyrimidin-6-yl]-2-(2,4,5-trifluorophenyl)cyclohexyl]carbamate (265 mg) and DDQ (111 mg) in 4 nm of dioxane was stirred for 4 h and the resulting product purified by chromatography on a Biotage Horizon® system (silica, gradient 10-35% ethyl acetate/dichloromethane) to give the title compound. LC-MS 549.3 (M+1). A portion of this product (20 mg) was dissolved in acetonitrile (2 mL), treated with trimethylsilyl iodide (0.2 mL), stirred for 30 min, and quenched with methanol (2 mL). The desired product was purified by preparative TLC (silica, 1:9:90 ammonium hydroxide:methanol:dichloromethane). LC-MS 415.3.

EXAMPLE 9

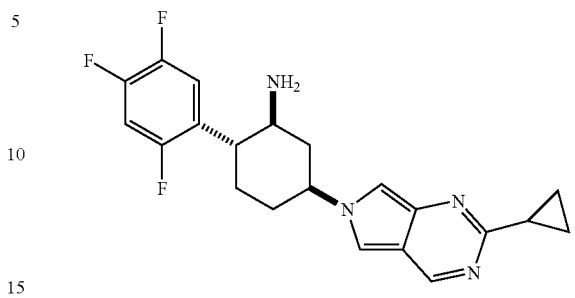

[(1S,2R,5S)-5-[2-Cyclopropyl-6H-pyrrolo[3,4-d]pyrimidin-6-yl]-2-(2,4,5-trifluorophenyl)cyclohexyl]amine A solution of [(1S,2R,5S)-5-[2-cyclopropyl-5,7-dihydro-6H-pyrrolo[3,4-d]pyrimidin-6-yl]-2-(2,4,5-trifluorophenyl)cyclohexyl]amine described in Example 2 (30.0 mg) in methanol (6 mL) was stirred with 10% palladium on carbon (6 mg) for seven days and the resulting product was purified by preparative TLC (silica, 7:93 methanol/dichloromethane) to give the title compound. LC-MS 387.3 (M+1).

EXAMPLE 10

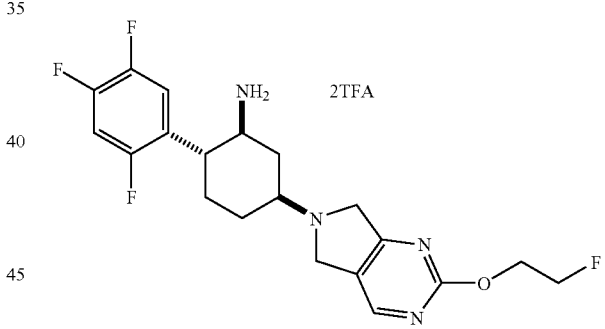

[(1S,2R,5S)-5-[2-(2-Fluoroethoxy)-5,7-dihydro-6H-pyrrolo[3,4-d]pyrimidin-6-yl]-2-(2,4,5-trifluorophenyl)cyclohexyl]amine, bis-trifluoroacetic acid salt Step A: Benzyl (1S,2R,5S)-5-[2-(2-fluoroethoxy)-5,7-dihydro-6H-pyrrolo[3,4-d]pyrimidin-6-yl]-2-(2,4,5-trifluorophenyl)cyclohexyl]carbamate To 106 mg (0.19 mmol) of Intermediate 8 in 6.3 mL of acetonitrile was added 0.11 mL (1.9 mmol) of 2-fluoroethanol and 309 mg (0.95 mmol) of cesium carbonate. The reaction mixture was refluxed for 5 min and cooled to 0° C., diluted with 2 mL of ethyl acetate and filtered. The filtrate was washed with two 2-mL portions of ethyl acetate, and the combined washings were concentrated in vacuo. The residue was purified by preparative thin layer chromatography using an Analtech® 1500 micron plate (ethyl acetate) to give the title compound as a white solid. LC/MS 545.2 (M+1).

Step B: [(1S,2R,5S)-5-[2-(2-Fluoroethoxy)-5,7-dihydro-6H-pyrrolo[3,4-d]pyrimidin-6-yl]-2-(2,4,5-trifluorophenyl)cyclohexyl]amine bis-trifluoroacetic acid salt To 44 mg (0.08 mmol) of the product from Step A at 0° C. in 2 mL of acetonitrile was added 0.11 mL (0.8 mmol) of trimethylsilyl iodide. The ice bath was immediately removed and the reaction mixture warmed to ambient temperature and stirred for 45 min. The reaction mixture was then cooled to 0° C. and diluted slowly with 1 mL of methanol, concentrated in vacuo and the residue purified by reverse phase HPLC (YMC Pro-C18 column, gradient elution, 0% to 65% acetonitrile/water with 0.1% TFA) to afford the title compound as a white solid. LC/MS 411.1 (M+1).

EXAMPLE 11

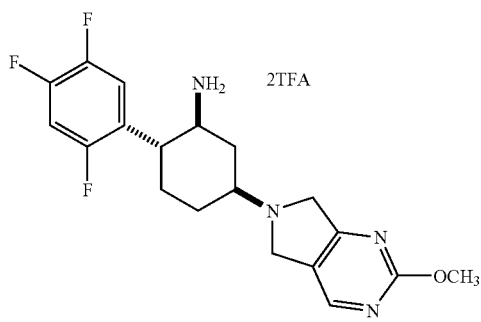

[(1S,2R,5S)-5-(2-Methoxy-5,7-dihydro-6H-pyrrolo[3,4-d]pyrimidin-6-yl)-2-(2,4,5-trifluorophenyl)cyclohexyl]amine, bis-trifluoroacetic acid salt Step A: Benzyl [(1S,2R,5S)-5-(2-methoxy-5,7-dihydro-6H-pyrrolo[3,4-d]pyrimidin-6-yl)-2-(2,4,5-trifluorophenyl)cyclohexyl]carbamate To 43 mg (0.076 mmol) of Intermediate 8 in 2 mL of methanol was added 99 mg (0.3 mmol) of cesium carbonate. The reaction mixture was stirred at ambient temperature for 1 h, diluted with 5 mL of ethyl acetate and poured into 5 mL of saturated aqueous brine solution. The layers were separated and the aqueous phase extracted with three 5-mL portions of ethyl acetate. The combined organic layers were dried with sodium sulfate, filtered and concentrated in vacuo. The residue was purified by preparative thin layer chromatography using an Analtech® 1500 micron plate (ethyl acetate) to give the title compound as a white solid. LC/MS 513.0 (M+1).

Step B: (1S,2R,5S)-5-(2-Methoxy-5,7-dihydro-6H-pyrrolo[3,4-d]pyrimidin-6-yl)-2-(2,4,5-trifluorophenyl)cyclohexanamine bis trifluoroacetic acid salt To 22 mg (0.04 mmol) of the product from Step A was added 2 mL (33% in acetic acid) of hydrobromic acid. The reaction mixture was stirred at ambient temperature for 30 min, concentrated in vacuo and the residue purified by reverse phase HPLC (YMC Pro-C18 column, gradient elution, 0% to 65% acetonitrile/water with 0.1% TFA) to afford the title compound as a yellow solid. LC/MS 379.1 (M+1).

EXAMPLE 12

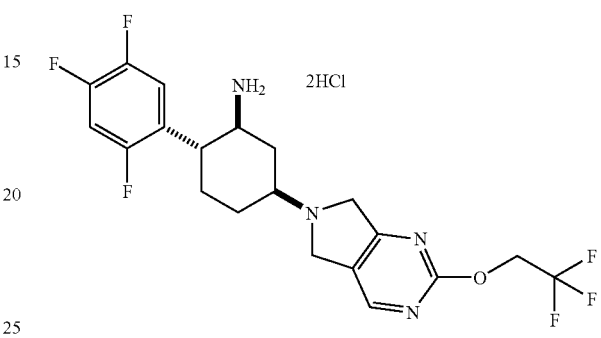

[(1S,2R,5S)-5-[2-(2,2,2-Trifluoroethoxy)-5,7-dihydro-6H-pyrrolo[3,4-d]pyrimidin-6-yl]-2-(2,4,5-trifluorophenyl)cyclohexyl]amine, dihydrochloride salt Step A: 2-(2,2,2-Trifluoroethoxy)-6,7-dihydro-5H-pyrrolo[3,4-d]pyrimidine To a solution of the tert-butyl 2-(methylsulfonyl)-5,7-dihydro-6H-pyrrolo[3,4-d]pyrimidine-6-carboxylate (300 mg) in dry acetonitrile (20 mL), 2,2,2-trifluoroethanol (1.8 mL) and cesium carbonate (815 mg) were added. The resulting mixture was stirred at room temperature for 1 h. The precipitate was removed by filtration. The solution was evaporated, and the resulting residue was purified on a Biotage Horizon® system (silica, gradient 35-65% ethyl acetate in hexanes). After concentration, tert-butyl 2-(2,2,2-trifluoroethoxy)-5,7-dihydro-6H-pyrrolo[3,4-d]pyrimidine-6-carboxylate was treated with HCl (4M in methanol) for 1 h. The residue was passed through an ion exchange resin (Strata-X-C™) and eluted with methanol containing 10% ammonium hydroxide to yield 2-(2,2,2-trifluoroethoxy)-6,7-dihydro-5H-pyrrolo[3,4-d]pyrimidine as the title compound. LC/MS 220.0 (M+1).

Step B: [(1S,2R,5S)-5-[2-(2,2,2-Trifluoroethoxy)-5,7-dihydro-6H-pyrrolo[3,4-d]pyrimidin-6-yl]-2-(2,4,5-trifluorophenyl)cyclohexyl]amine dihydrochloride salt The title compound was made by essentially following the same reductive amination and deprotection procedures described for Example 2. LC-MS 447.00 (M+1).

Following essentially the procedures outlined for Examples 1-12, the following additional Examples listed in Table 2 were prepared.

TABLE 2

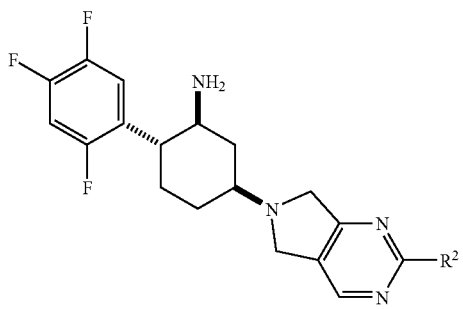

| Example | R² | MS (M + 1) |
|---------|-----|-----------|
| 13 | —OCH₂CHF₂ | 429.0 |
| 14 | —CN | 374.4 |
| 15 | 1H-tetrazol-5-yl | 417.3 |
| 16 | —CH₂CONH₂ | 407.5 |
| 17 | —CONH₂ | 392.4 |
| 18 | —CO₂H | 393.1 |
| 19 | —CO₂CH₂CH₃ | 421.1 |
| 20 | —CONHtBu | 448.2 |
| 21 | —OCH₂CH₂OH | 409.4 |
| 22 | —OCH₂CH₃ | 393.3 |

EXAMPLE OF A PHARMACEUTICAL FORMULATION

As a specific embodiment of an oral pharmaceutical composition, a 100 mg potency tablet is composed of 100 mg of any of Examples 1-22, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

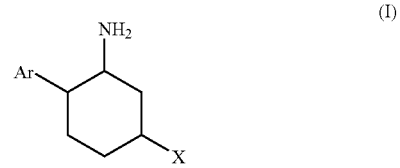

(I)

or a pharmaceutically acceptable salt thereof; wherein
each n is independently 0, 1, 2, or 3;
X is selected from the group consisting of:

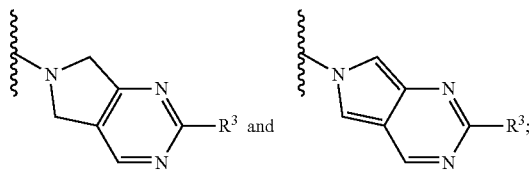

Ar is phenyl unsubstituted or substituted with one to five $R^1$ substituents;
each $R^1$ is independently selected from the group consisting of
halogen,
cyano,
hydroxy,
$C_{1-6}$ alkyl, unsubstituted or substituted with one to five halogens,
$C_{1-6}$ alkoxy, unsubstituted or substituted with one to five halogens, carboxy,
$C_{1-6}$ alkyloxycarbonyl,
amino,
$NHR^2$,
$NR^2R^2$,
$NHSO_2R^2$,
$NR^2SO_2R^2$,
$NHCOR^2$,
$NR^2COR^2$,
$NHCO_2R^2$,
$NR^2CO_2R^2$,
$SO_2R^2$,
$SO_2NH_2$,
$SO_2NHR^2$, and
$SO_2NR^2R^2$;
each $R^2$ is independently $C_{1-6}$ alkyl, unsubstituted or substituted with one to five substituents independently selected from halogen, $CO_2H$, and $C_{1-6}$ alkyloxycarbonyl;
$R^3$ is selected from the group consisting of
hydrogen,
hydroxy,
halogen,
cyano,
$CO_2H$,
$NR^4R^5$,
$CONR^4R^5$,
$CH_2CONR^4R^5$,
$OCONR^4R^5$,
$SO_2NR^4R^5$,
$SO_2R^6$,
$NR^7SO_2R^6$,
$NR^7CONR^4R^5$,
$NR^7COR^6$,
$NR^7CO_2R^6$, 1H-tetrazol-5-yl,
$C_{1-6}$ alkyloxycarbonyl,
$C_{1-6}$ alkyl unsubstituted or substituted with hydroxy or one to five halogens,
$C_{1-6}$ alkoxy unsubstituted or substituted with hydroxy or one to five halogens,
$C_{1-6}$ alkylthio,
$C_{1-6}$ alkylsulfonyl, and
$(CH_2)_n$-$C_{3-6}$ cycloalkyl, wherein cycloalkyl is unsubstituted or substituted with one to three substituents independently selected from halogen, hydroxy, $C_{1-4}$ alkyl, and $C_{1-4}$ alkoxy, wherein alkyl and alkoxy are unsubstituted or substituted with one to five halogens;
wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
$R^4$ and $R^5$ are each independently selected from the group consisting of
hydrogen,
$(CH_2)_n$-phenyl,
$(CH_2)_n$-$C_{3-6}$ cycloalkyl, and
$C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;
each $R^6$ is independently $C_{1-6}$ alkyl, wherein alkyl is unsubstituted or substituted with one to five substituents independently selected from halogen and hydroxyl; and
$R^7$ is hydrogen or $R^6$.

2. The compound of claim 1 wherein each $R^1$ is independently selected from the group consisting of fluorine, chlorine, bromine, methyl, trifluoromethyl, and trifluoromethoxy.

3. The compound of claim 1 of structural formulae Ia and Ib having the indicated stereochemical configuration at the two stereogenic cyclohexane carbon atoms marked with an *:

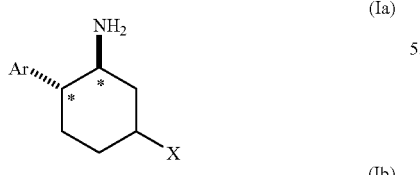
(Ia)

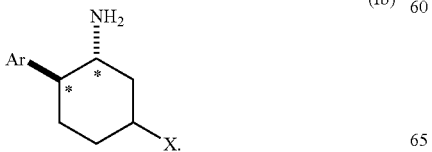
(Ib)

4. The compound of claim 3 of structural formula Ia having the indicated absolute stereochemical configuration at the two stereogenic cyclohexane carbon atoms marked with an *:

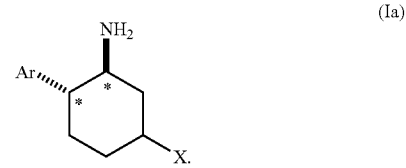
(Ia)

5. The compound of claim 3 of structural formulae Ic and Id having the indicated stereochemical configuration at the three stereogenic cyclohexane carbon atoms marked with an *:

(Ic)

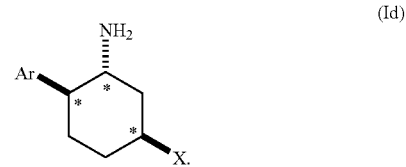
(Id)

6. The compound of claim 5 of structural formula Ic having the indicated absolute stereochemical configuration at the three stereogenic cyclohexane carbon atoms marked with an *:

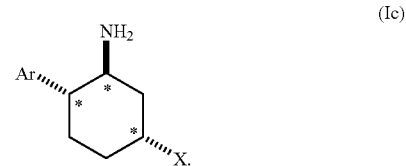
(Ic)

7. The compound of claim 3 of structural formulae Ie and If having the indicated stereochemical configuration at the three stereogenic cyclohexane carbon atoms marked with an *:

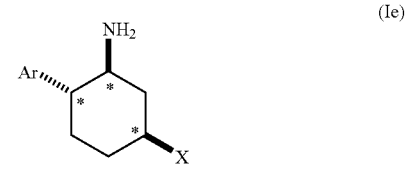
(Ie)

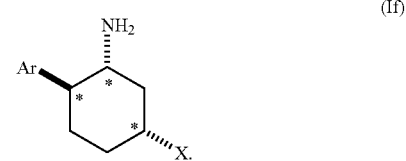
(If)

8. The compound of claim 7 of structural formula Ie having the indicated absolute stereochemical configuration at the three stereogenic cyclohexane carbon atoms marked with an *:

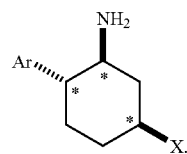

(Ie)

9. The compound of claim 8 of structural formula Ig:

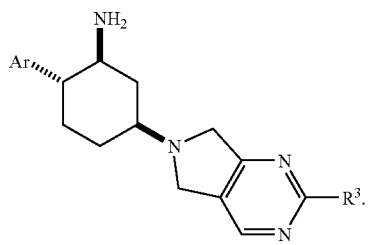

(Ig)

10. The compound of claim 8 of structural formula Ih:

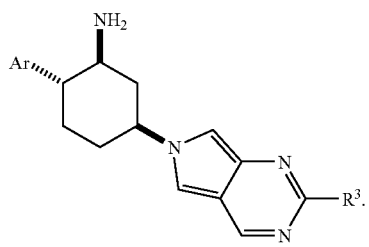

(Ih)

11. The compound of claim 8 wherein $R^3$ is selected from the group consisting of:
hydrogen,
cyano,
$CO_2H$,
1H-tetrazol-5-yl,
$C_{1-3}$ alkyloxycarbonyl,
$CONR^4R^5$,
$CH_2CONR^4R_5$,
$C_{1-3}$ alkyl, wherein alkyl is unsubstituted or substituted with one to five fluorines,
$C_{1-3}$ alkoxy, wherein alkoxy is unsubstituted or substituted with hydroxy or one to five fluorines, and
$C_{3-6}$ cycloalkyl, wherein cycloalkyl is unsubstituted or substituted with one to three substituents independently selected from halogen, hydroxy, $C_{1-4}$ alkyl, and $C_{1-4}$ alkoxy, wherein alkyl and alkoxy are unsubstituted or substituted with one to five halogens.

12. The compound of claim 11 of the structural formula selected from the group consisting of:

| $R^1$ | $R^2$ |
|---|---|
| 2-F, 5-F | Me |
| 2-F, 5-F | cyclopropyl |
| 2-F, 5-F | $CF_3$ |
| 2-F, 4-F, 5-F | H |
| 2-F, 4-F, 5-F | Me |
| 2-F, 4-F, 5-F | cyclopropyl |
| 2-F, 4-F, 5-F | $CF_3$ |
| 2-F, 4-F, 5-F | H |
| 2-F, 4-F, 5-F | —$OCH_2CH_2F$ |
| 2-F, 4-F, 5-F | —$OCH_3$ |
| 2-F, 4-F, 5-F | —$OCH_2CF_3$ |
| 2-F, 4-F, 5-F | —$OCH_2CHF_2$ |
| 2-F, 4-F, 5-F | —CN |
| 2-F, 4-F, 5-F | 1H-tetrazol-5-yl |
| 2-F, 4-F, 5-F | —$CH_2CONH_2$ |
| 2-F, 4-F, 5-F | —$CONH_2$ | or a pharmaceutically acceptable salt thereof.

13. A pharmaceutical composition which comprises a compound of claim 1 and a pharmaceutically acceptable carrier.

14. The pharmaceutical composition of claim 13 additionally comprising metformin.

15. A method of treating non-insulin dependent (Type 2) diabetes in a mammal in need thereof which comprises the administration to the mammal of a therapeutically effective amount of a compounds of claim 1.

* * * * *